United States Patent
Hourani et al.

(10) Patent No.: US 12,226,728 B2
(45) Date of Patent: *Feb. 18, 2025

(54) DETOXIFICATION DEVICE HAVING HEATED FILTER FOR KILLING PATHOGENS

(71) Applicant: UNIVERSITY OF HOUSTON SYSTEM, Houston, TX (US)

(72) Inventors: Monzer A. Hourani, Houston, TX (US); Zhifeng Ren, Houston, TX (US); Luo Yu, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/889,596

(22) Filed: Aug. 17, 2022

(65) Prior Publication Data

US 2023/0124578 A1    Apr. 20, 2023

Related U.S. Application Data

(63) Continuation of application No. 17/118,379, filed on Dec. 10, 2020, now Pat. No. 11,446,600.

(51) Int. Cl.
*B01D 46/00*    (2022.01)
*A61L 9/014*    (2006.01)
(Continued)

(52) U.S. Cl.
CPC .......... *B01D 46/4263* (2013.01); *A61L 9/014* (2013.01); *A61L 9/16* (2013.01);
(Continued)

(58) Field of Classification Search
CPC .............. B01D 46/4263; B01D 46/448; B01D 46/444; B01D 46/0028; B01D 46/4245;
(Continued)

(56) References Cited

U.S. PATENT DOCUMENTS 2,594,101 A    4/1952    Volker
2,849,589 A    8/1958    Lancaster
(Continued)

FOREIGN PATENT DOCUMENTS

CN    101929255 A    12/2010
CN    103002606 A    3/2013
(Continued)

OTHER PUBLICATIONS

First Office Action in counterpart Japanese Appl. 2020-129200, dated Jun. 8, 2021.
(Continued)

*Primary Examiner* — Minh Chau T Pham
(74) *Attorney, Agent, or Firm* — Blank Rome LLP

(57) ABSTRACT

A detoxification device for removing pathogens from air within an environment. The detoxification device may include a filtration media for catching and retaining particles larger than about 0.3 micrometers (µm) with an efficiency of at least 99%. The detoxification device may also include a heating element having a metallic foam. The heating element may be heated upon application of an electrical current to the heating element. The heating element may, upon being heated, heat the filtration media to a target temperature that is effective to kill a pathogen.

18 Claims, 7 Drawing Sheets

(51) Int. Cl.
| | |
|---|---|
| *A61L 9/16* | (2006.01) |
| *B01D 39/16* | (2006.01) |
| *B01D 46/42* | (2006.01) |
| *B01D 46/44* | (2006.01) |
| *B01D 46/52* | (2006.01) |
| *F24F 8/108* | (2021.01) |
| *H05B 1/02* | (2006.01) |
| *H05B 3/12* | (2006.01) |

(52) U.S. Cl.
CPC ..... B01D 39/1623 (2013.01); B01D 46/0002 (2013.01); B01D 46/0028 (2013.01); B01D 46/444 (2013.01); B01D 46/521 (2013.01); F24F 8/108 (2021.01); H05B 1/0288 (2013.01); H05B 3/12 (2013.01); *A61L 2209/14* (2013.01); *A61L 2209/16* (2013.01); *A61L 2209/22* (2013.01); *B01D 2239/1216* (2013.01); *B01D 2279/40* (2013.01); *B01D 2279/50* (2013.01); *B01D 2279/65* (2013.01)

(58) Field of Classification Search
CPC .............. B01D 46/429; B01D 39/2027; B01D 2279/50; B01D 2279/65; B60H 3/0608; F24F 3/1903; F24F 2003/1667; F24F 2221/34; A61L 9/20; A61L 2209/11; A61L 2209/15
USPC .............. 55/385.2, 385.1, DIG. 34; 454/187; 422/121, 186.04, 186.3
See application file for complete search history.

(56) References Cited

U.S. PATENT DOCUMENTS

| | | | |
|---|---|---|---|
| 3,395,972 A | 8/1968 | Hardison | |
| 4,661,126 A | 4/1987 | Inagami et al. | |
| 4,707,167 A * | 11/1987 | Saito | B01D 46/523 55/385.2 |
| 5,180,409 A | 1/1993 | Fischer | |
| 5,192,346 A | 3/1993 | Kowalczyk | |
| 5,837,207 A | 11/1998 | Summers | |
| 6,464,760 B1 | 10/2002 | Sham et al. | |
| 6,500,387 B1 | 12/2002 | Bigelow | |
| 6,680,028 B1 | 1/2004 | Harris | |
| 6,716,406 B2 | 4/2004 | Reisfeld et al. | |
| 7,083,663 B2 | 8/2006 | Shih | |
| 7,270,591 B2 | 9/2007 | Deshpande et al. | |
| 7,625,277 B2 | 12/2009 | Palmer | |
| 8,263,012 B2 | 9/2012 | Hay et al. | |
| 8,444,747 B2 | 5/2013 | Kristensson | |
| 8,529,830 B2 | 9/2013 | Zhou et al. | |
| 8,772,744 B1 | 7/2014 | Liu | |
| 10,117,961 B2 | 11/2018 | Horne et al. | |
| 10,471,170 B2 | 11/2019 | Lee | |
| 11,446,600 B2 * | 9/2022 | Hourani | F24F 3/16 |
| 2004/0003581 A1 | 1/2004 | Lim | |
| 2004/0041564 A1 | 3/2004 | Brown | |
| 2004/0047776 A1 | 3/2004 | Thomsen | |
| 2005/0092181 A1 * | 5/2005 | Shih | H05B 3/12 55/490.1 |
| 2008/0031783 A1 | 2/2008 | Briggs et al. | |
| 2008/0086994 A1 | 4/2008 | Descotes et al. | |
| 2008/0121823 A1 | 5/2008 | Goel et al. | |
| 2010/0032055 A1 | 2/2010 | Sangi | |
| 2010/0323603 A1 | 12/2010 | Lans | |
| 2011/0308522 A1 | 12/2011 | Kimm | |
| 2012/0192717 A1 | 8/2012 | Gonze | |
| 2012/0196147 A1 | 8/2012 | Rabiei | |
| 2013/0256631 A1 | 10/2013 | Khan et al. | |
| 2013/0294968 A1 | 11/2013 | Owen et al. | |
| 2014/0369894 A1 | 12/2014 | Hingorani et al. | |
| 2015/0092181 A1 | 4/2015 | Nishita | |
| 2015/0359921 A1 | 12/2015 | Palmer | |
| 2016/0067647 A1 | 3/2016 | Tate | |
| 2017/0028820 A1 | 2/2017 | Walsh | |
| 2017/0139386 A1 | 5/2017 | Pillai et al. | |
| 2017/0292797 A1 | 10/2017 | Roberge | |
| 2018/0050124 A1 | 2/2018 | Lee | |
| 2019/0063763 A1 | 2/2019 | Kleinberger et al. | |
| 2019/0083673 A1 | 3/2019 | Munn | |
| 2020/0009286 A1 | 1/2020 | Zarcone et al. | |
| 2020/0086257 A1 * | 3/2020 | Liu | B01D 46/24 |
| 2020/0182496 A1 | 6/2020 | Xiao et al. | |
| 2020/0300460 A1 | 9/2020 | Rush, III | |
| 2021/0339183 A1 | 11/2021 | Hourani et al. | |
| 2021/0339184 A1 | 11/2021 | Hourani et al. | |
| 2023/0119976 A1 | 4/2023 | Maletich | |

FOREIGN PATENT DOCUMENTS

| | | |
|---|---|---|
| CN | 203731560 U | 7/2014 |
| CN | 204404388 U | 6/2015 |
| CN | 204478279 U | 7/2015 |
| CN | 205593084 U | 9/2016 |
| CN | 206919206 U | 1/2018 |
| CN | 206973703 U | 2/2018 |
| CN | 206973773 U | 2/2018 |
| CN | 108779925 A | 11/2018 |
| CN | 108981014 A | 12/2018 |
| CN | 209524549 U | 10/2019 |
| CN | 111043670 A | 4/2020 |
| JP | 50128324 | 10/1975 |
| JP | 60193517 | 10/1985 |
| JP | 61171514 A | 8/1986 |
| JP | 01210010 A | 8/1989 |
| JP | 09126551 A | 5/1997 |
| JP | H09126551 A | 5/1997 |
| JP | 2004508163 A | 3/2004 |
| JP | 2004130173 A | 4/2004 |
| JP | 2005013687 A | 1/2005 |
| JP | 2005137871 A | 6/2005 |
| JP | 200744432 A | 2/2007 |
| JP | 2011224121 A | 11/2011 |
| JP | 2015104400 A | 6/2015 |
| JP | 2018509499 A | 4/2018 |
| KR | 20100036438 A | 4/2010 |
| KR | 20170035481 A | 3/2017 |
| KR | 20180000833 A | 1/2018 |
| WO | 200220064 A2 | 3/2002 |
| WO | 2004006969 A1 | 1/2004 |
| WO | 2005075000 A1 | 8/2005 |
| WO | 2016135257 A2 | 9/2016 |
| WO | 2019056323 A1 | 3/2019 |
| WO | 2019204570 A1 | 10/2019 |
| WO | 2021221698 A1 | 11/2021 |
| WO | 2021221699 A1 | 11/2021 |

OTHER PUBLICATIONS

First Office Action in counterpart Japanese Appl. 2020-129203, dated May 11, 2021.
International Search Report and Written Opinion in PCT Appln PCT/US20/35608, dated Oct. 2, 2020.
International Search Report and Written Opinion in PCT Appln PCT/US20/35607, dated Sep. 8, 2020.
Yu, L. et al., "Catching and killing of airborne SARS-CoV-2 to control spread of COVID-19 by a heated air disinfection system," Materials Today Physics, 15 (2020) 100249, Jul. 7, 2020, 5-pgs.
Search Report and Written Opinion in counterpart Singapore Appl. 10202007442S, dated Sep. 10, 2021, 11-pgs.
High-Performance Alloys for Resistance to Aqueous Corrosion, 2001, obtained from URL at https://www.parrinst.com/wpcontent/uploads/downloads/2011/07/Parr_Inconel-Incoloy-Monel-Nickel-Corrosion-Info.pdf.
Search Report and Written Opinion in counterpart Singapore Appl. 10202007444V, dated Jan. 20, 2022, 10-pgs.
First Office Action in counterpart Japanese Appl. 2020-129200, mailed Jun. 8, 2021.
First Office Action in counterpart Japanese Appl. 2020-129203, mailed May 11, 2021.

(56) References Cited

OTHER PUBLICATIONS

First Examination Report in counterpart GCC Appl. 2020-40143, dated Aug. 31, 2021, 4-pgs.
First Examination Report in counterpart GCC Appl. 2020-40144, dated Aug. 31, 2021, 4-pgs.
First Office Action in counterpart Chinese Appl. 202010849987.X, dated Jul. 29, 2021, 6-pgs.
First Office Action in counterpart Chinese Appl. 202010849059.3, dated Jul. 29, 2021, 6-pgs.
Second Notice of Reasons for Refusal in counterpart JP Appl. 2020-129203, dated Jan. 11, 2022, 11-pgs.
Brown, "This portable furnace could stop coronavirus in its tracks" Mar. 18, 2020.
International Search Report and Written Opinion in PCT Appln PCT/US20/35608, mailed Oct. 2, 2020.
International Search Report and Written Opinion in PCT Appln PCT/US20/35607, mailed Sep. 8, 2020.
Second Notice of Reasons for Refusal in counterpart JP Appl. 2020-129200 dated Mar. 8, 2022, 7 pages.
Extended European Search Report issued Dec. 6, 2023 in counterpart European Patent Application No. 20933580.1 (10 pages).
Office Action issued Feb. 26, 2024 in corresponding U.S. Appl. No. 18/213,644 (10 pages).
Office Action in U.S. Appl. No. 17/118,379, mailed Apr. 7, 2021, 8-pgs.
Final Office Action in U.S. Appl. No. 17/118,379, mailed Jul. 20, 2021, 9-pgs.
Office Action in U.S. Appl. No. 16/883,977, mailed Feb. 23, 2024, 9-pgs.

* cited by examiner

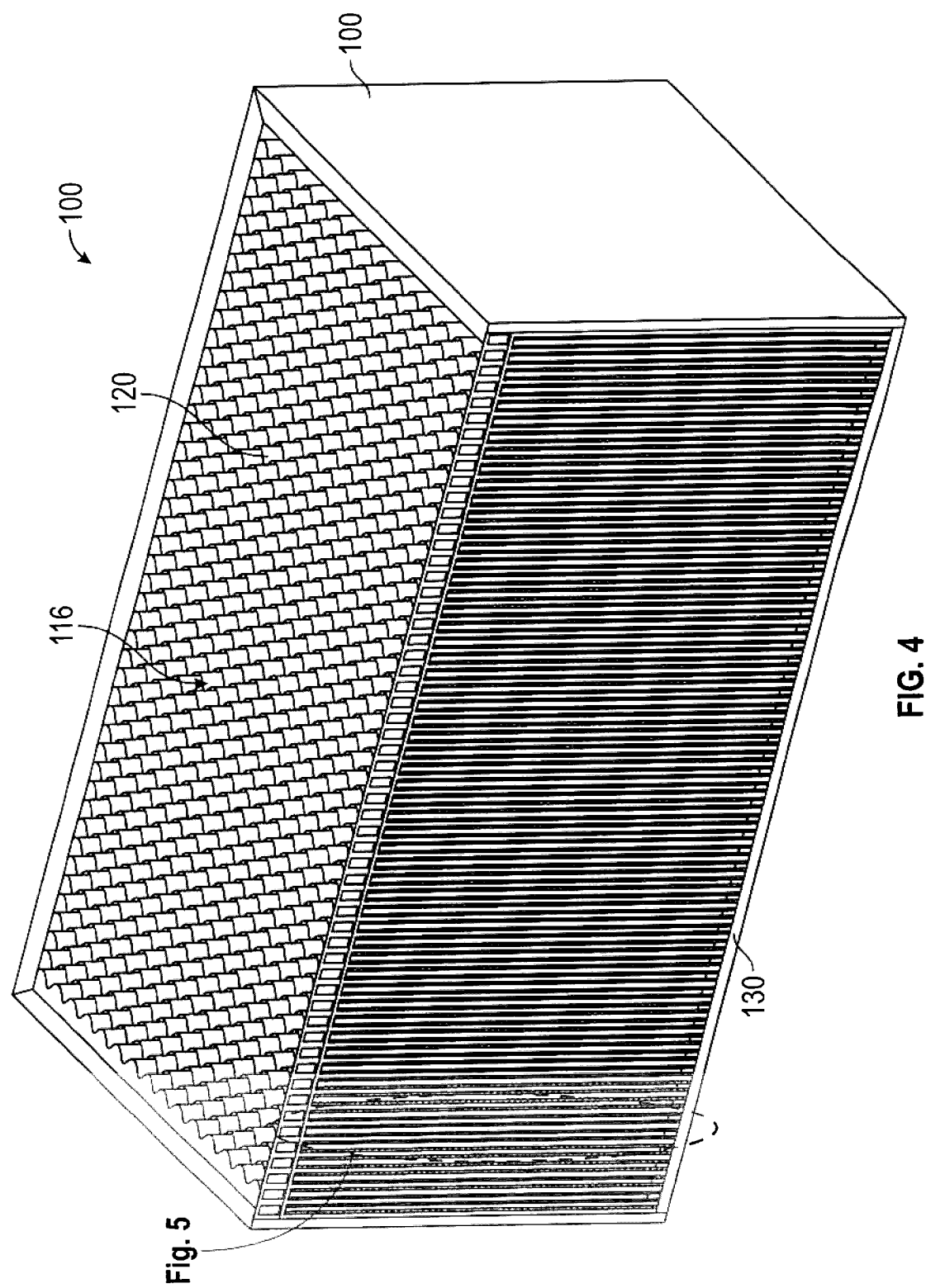

DETOXIFICATION DEVICE HAVING HEATED FILTER FOR KILLING PATHOGENS

CROSS-REFERENCE TO RELATED APPLICATIONS

This is a continuation of application U.S. application Ser. No. 17/118,379 filed Dec. 10, 2020, now U.S. Pat. No. 11,446,600, which is incorporated herein by reference in its entirety. This application is also co-pending with U.S. application Ser. No. 16/883,977 filed May 26, 2020 and U.S. application Ser. No. 16/883,981 filed May 26, 2020, both of which are incorporated herein by reference in their entireties and both which claim the benefit of U.S. Provisional Application Ser. No. 63/018,442 filed Apr. 30, 2020 and U.S. Provisional Application Ser. No. 63/018,448 filed Apr. 30, 2020, both of which are also incorporated herein by reference in their entireties.

TECHNICAL FIELD

The subject matter set forth in the appended claims relates generally to systems, devices, and methods for detoxification of air, particularly, for removing pathogens from the air.

CROSS-REFERENCE TO RELATED APPLICATIONS

Not applicable.

BACKGROUND

Systems, apparatuses, and methods for air filtration are used in heating, ventilating, and air conditioning (HVAC) systems to remove dust, pollen, mold, particulates, and the like from the air being moved through a facility. The filters used for the filtration can come in a number of forms and can be configured to filter particles of a given size with a given efficiency.

For example, high-efficiency particulate air (HEPA) filters are commonly used in cleanrooms, operating rooms, pharmacies, homes, etc. These filters can be made of different types of media, such as fiberglass media, expanded polytetrafluoroethylene (ePTFE) media, etc., and may include activated carbon-based materials. In general, HEPA filters can filter over 99 percent of particles with a diameter of a given size (e.g., 0.3 microns or size). However, even with such efficiency, HEPA filters may be ineffective to stop pathogens (virons, bacteria, etc.).

Also, ultraviolet (UV) germicidal lights can stop pathogens, such as bacteria, viruses, and mold. The UV germicidal lights produce ultraviolet radiation, which can then damage the genetic material of the microorganisms. The damage may kill the pathogen or make them unable to reproduce. Extended exposure to the UV radiation can also break down pathogens that have deposited on an irradiated surface. One example of an ultraviolet system includes an upper room air ultraviolet germicidal irradiation (UVGI) system.

Although existing systems for filtration and germicidal irradiation can be effective in treating air to remove particulates and damage pathogens, there is a continuing need to detoxify and/or purify air in facilities, such as homes, workspaces, hospitals, nursing homes, and the like, to reduce the spread of pathogens, such as bacteria, viruses, and molds, even more.

In particular, the 2019 novel coronavirus disease (COVID-19) is a virus of global health significance caused by infection of severe acute respiratory syndrome coronavirus 2 (SARS-CoV-2). COVID-19 is thought to spread from person to person in close contact through respiratory droplets. Studies show the virus can survive for hours at a time and can be persistently carried by airflow. For example, COVID-19 (Sars-CoV-2) may survive in droplets for up to three hours after being expelled into the air, and convection in the air is thought to be the primary mechanism for the spread of the infection. Accordingly, droplet-spray and convection can drive direct airborne infection, and social distancing can be ineffective for enclosed environments where people spend substantial time together.

As there is no current cure for COVID-19, environmental detoxification strategies can help slow the spread of the virus. Unfortunately, current systems to treat circulated air are expensive and use primarily UV germicidal light. These products require professional installation, are not accessible to the general public per se, and have not been used to kill COVID-19.

For these reasons, the subject matter of the present disclosure is directed to overcoming, or at least reducing the effects of, one or more of the problems set forth above.

BRIEF SUMMARY

In some embodiments is a detoxification device for removing pathogens from air within an environment. The detoxification device may comprise a filtration media configured to catch and retain particles larger than about 0.3 micrometers (μm) with an efficiency of at least 99%. The detoxification device may also comprise a heating element comprising a metallic foam. The heating element may be configured to be heated upon application of an electrical current to the heating element. The heating element may be configured, upon being heated, to heat the filtration media to a target temperature that is effective to kill a pathogen.

In some embodiments, the filtration media may be characterized as withstanding a temperature of at least 200° C. without degradation or diminishment of its filtration capacity. Also, in some embodiments, the metallic foam may comprise an alloy comprising at least 99% by weight of an alloy comprising chromium and nickel. For example, the alloy may be stainless steel. The metallic foam may include a plurality of open-cell pores a least partially defining a plurality of flow-paths through the heating element. For example, the metallic foam may exhibit a porosity of from about 80 pores per square inch to about 120 pores per square inch.

Also, in some embodiments is a method for removing pathogens from within an environment. The method may comprise determining that air flow is not being conducted through a detoxification device. The detoxification device may comprise a filtration media configured to catch and retain particles larger than about 0.3 micrometers (μm) with an efficiency of at least 99%. The detoxification device may also comprise a heating element comprising a metallic foam. The method may also comprise, based upon the determination that air flow is not being conducted through the detoxification device, heating the heating element so that, upon the heating element being heated, the filtration media is heated to a target temperature that is effective to kill a pathogen.

The foregoing summary is not intended to summarize each potential embodiment or every aspect of the present disclosure.

BRIEF DESCRIPTION OF THE DRAWINGS

FIG. 4 illustrates a cutaway perspective view of a detoxification device of the present disclosure.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that will enable a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation may assume a particular frame of reference although, as should be recognized by those skilled in the art, this frame of reference is merely a descriptive expedient rather than a strict prescription.

Figure 1:
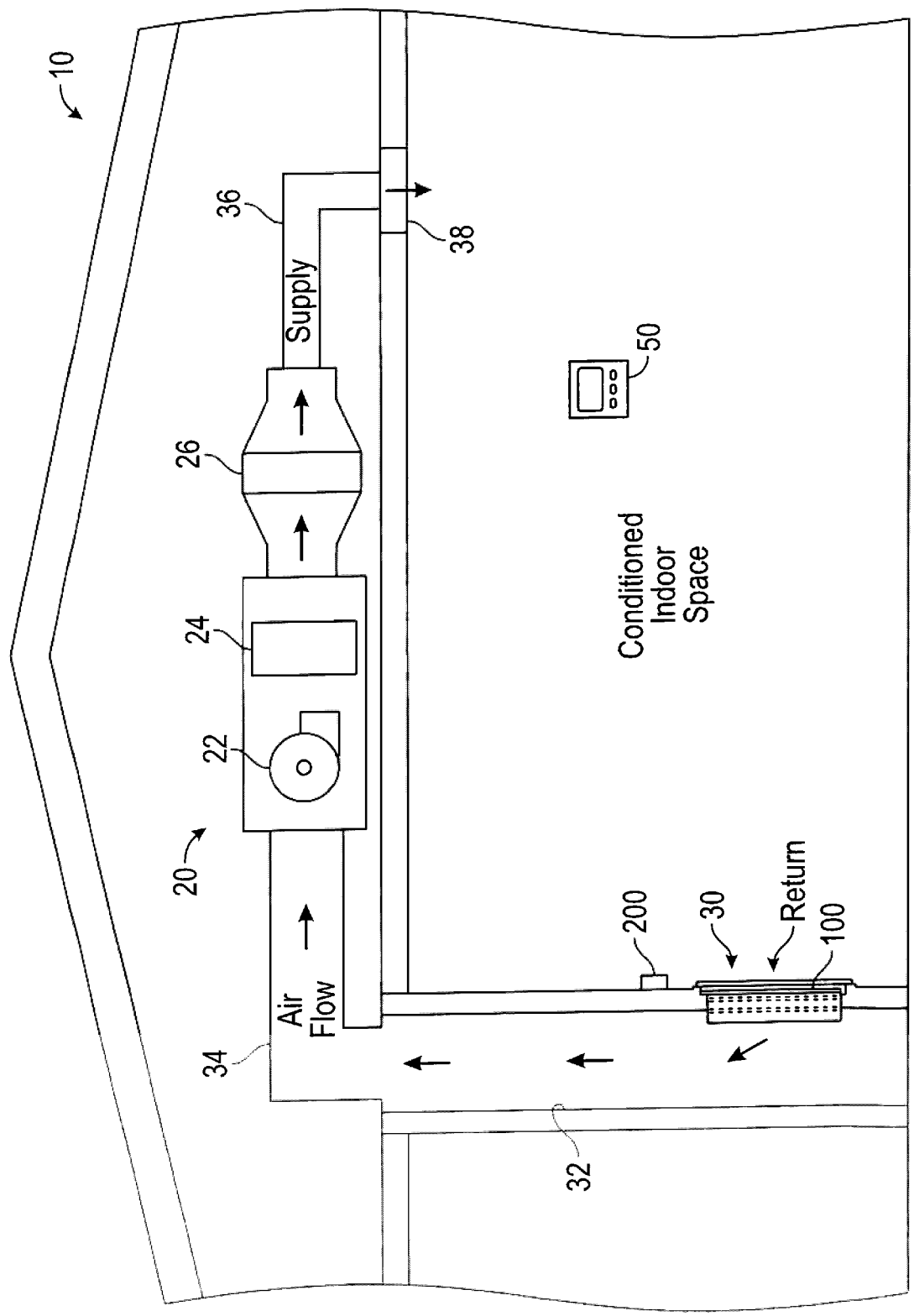
FIG. 1 illustrates a facility having an air handling system having a detoxification device according to the present disclosure.

Referring to FIG. 1, an environment, which may be a facility 10 such as a home, hospital, office space, airport terminal, church, or other enclosed environment, has an air handling system 20. In the embodiment of FIG. 1, the air handling system 20 is illustrated as a heating, ventilating, and air conditioning (HVAC) system although, in other embodiments, various other the air handling system configurations can be used. For example, in the embodiment of FIG. 1, the system 20 (e.g., an HVAC system) includes air returns 30, chases 32, and return ducts 34 generally arranged to direct drawn return air from an indoor space to a blower 22, heat exchanger 24, and cooling unit 26 of the HVAC system 20. In turn, the HVAC system 20 provides conditioned supply air to the space through supply ducts 36, vents 38, and the like. The heat exchanger 24 can include an electric or gas furnace for heating the air. The cooling unit 26 can be an evaporator connected in a cooling circuit to other conventional components outside the facility, such as a condenser, compressor, expansion valve, and related components.

As will be disclosed herein, the detoxification device 100 does not significantly alter the temperature of the air being treated, for example, although the detoxification device may tend to only minimally heat the air. For this reason, the detoxification device 100 may be disposed in the return air upstream of the cooling unit 26. This can allow some of the heat to be dissipated in the air flow before being cooled by the cooling unit 26. Alternatively, in some embodiments, the detoxification device 100 may be disposed downstream of the cooling unit 26 and/or heat exchanger and the cooling unit 26 and/or heat exchanger may be operated to account for any heat added to the air by operation of the detoxification device 100. For example, when heating the indoor space, the detoxification device 100 may simply add to the heat provided by the HVAC system 20.

In the embodiment of FIG. 1, one or more detoxification devices 100 are integrated with or incorporated into the HVAC system 20. As disclosed herein, the one or more detoxification devices 100 are used in the facility to detoxify and/or purify the air flow. In one arrangement, for example, as shown in the embodiment of FIG. 1, the detoxification device 100 is disposed in the air return 30 of the HVAC system 20, through which return air is drawn to pass through the conditioning elements of the HVAC system 20. In some embodiments, each air return 30 in a facility may have such a detoxification device 100 so return air is drawn through the detoxification device 100 during operation of the HVAC system 20. Because HVAC systems 20 use a number of different filters of various sizes, the detoxification device 100 can have dimensions to suit various filter sizes.

Figure 2A:
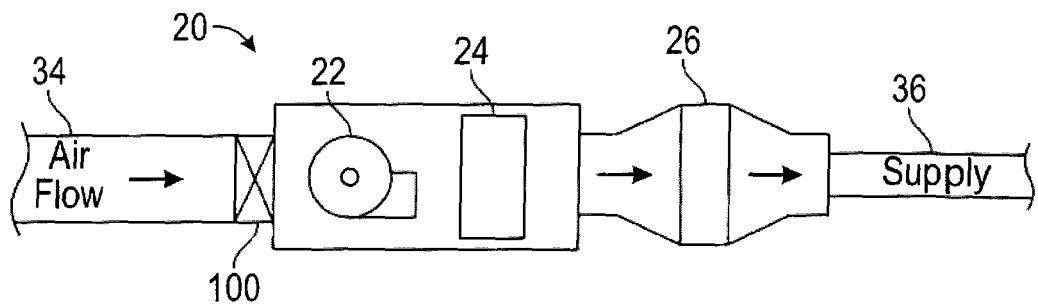
FIGS. 2A, 2B, 2C, 2D, and 2E illustrate other arrangements of the disclosed detoxification device used with various air handling systems.
Figure 2B:
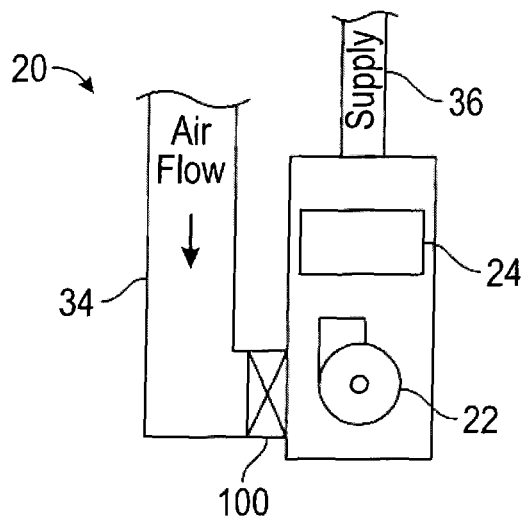
Figure 2C:
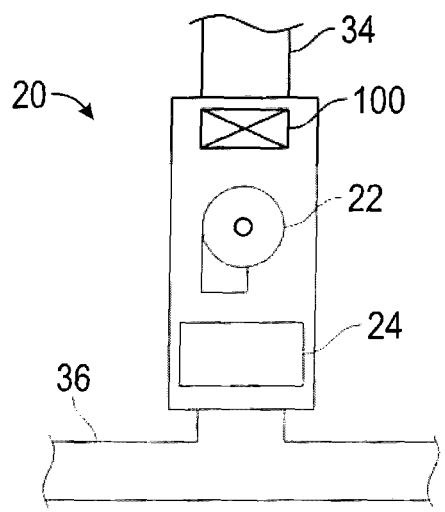

Although FIG. 1 shows the detoxification device 100 disposed at the return 30 for the chase 32 of the air handling system 20, other arrangements can be used. Generally, the detoxification device 100 may be sized to be integrated into a typical opening configured to receive a conventional air filter present in an air handling system (e.g., 14-20 in×25 in) as commercially available. For example, in some embodiments, referring to FIG. 2A, the detoxification device 100 may be disposed immediately upstream of the blower 22 and other components of an HVAC system 20 having a heat exchanger 24 configured as a horizontal furnace. Referring to FIG. 2B, in some embodiments the detoxification device 100 may be disposed adjacent the blower 22 and other components of an HVAC system 20 having a heat exchanger 24 configured as an upflow furnace. Finally, FIG. 2C shows the detoxification device 100 disposed above the blower 22 and other components of an HVAC system having a heat exchanger 24 configured as a downflow furnace. These and other configurations can be used. The heat exchanger 24 can use gas burners or electric heating elements.

Figure 2D:
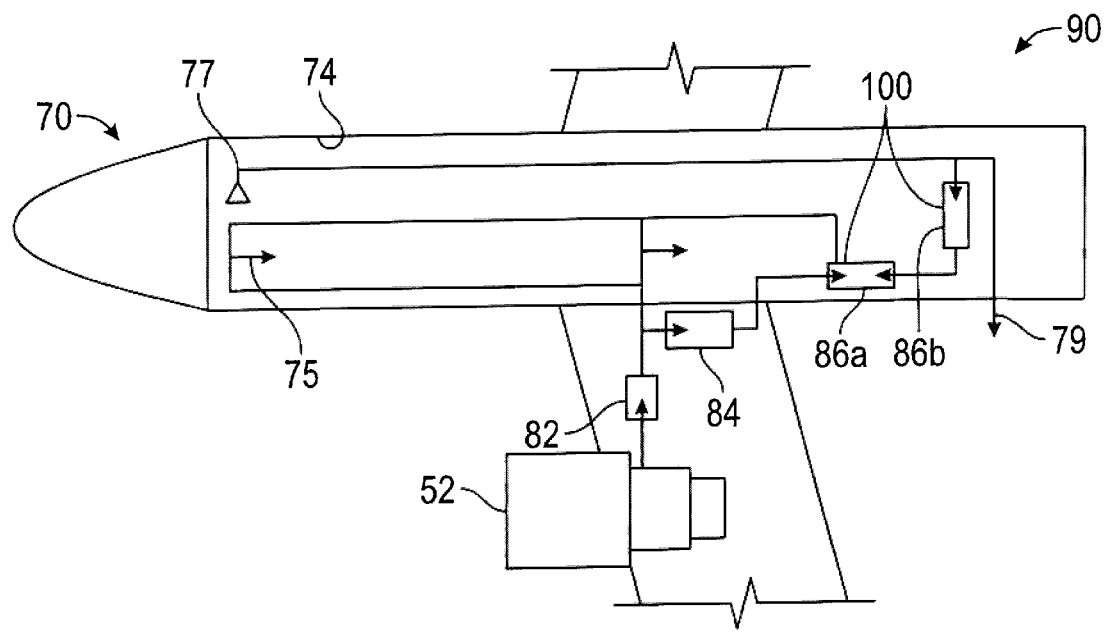

Additionally or alternatively, in some other embodiments, the detoxification device 100 may be similarly employed in various other embodiments. For example, FIG. 2D illustrates an air handling system 80 in an airplane 70 having a detoxification device 100 of the present disclosure. In the airplane 70, the air in the cabin 74 may be changed 20 to 30 times per hour with about half of the air being recycled through filters. Because the cabin 74 is pressurized, outside air enters an inlet 82 of the system 80 at high temperature and pressure from the engines 72. The hot and compressed air reaches the air conditioning units 84 for the plane 70 where the air is cooled considerably. For heating, some of the input air can enter the cabin 74 though the overhead outlets 75. For cooling, the air from the conditioning unit 84 passes to a mixing manifold 86a in which the cooled outside air may be combined with cabin air in about a 50/50 ratio. The mixed air from the mixing manifold 86a can then be circulated through the cabin 74 via the overhead outlets 75. A portion of the air in the cabin 74 from inlets 77 is then discharged from outlet 79 in an equal amount to the outside air entering the cabin 74 to maintain a balance, and another portion of the cabin air though a buffer manifold 86b is recirculated in the mixing chamber 86a. Because the outside air is new, the detoxification device 100 of the present disclosure may be placed at the mixing manifold 86a and/or the buffer manifold 86b of the air handling system 80 to treat the recycled cabin air.

Figure 2E:
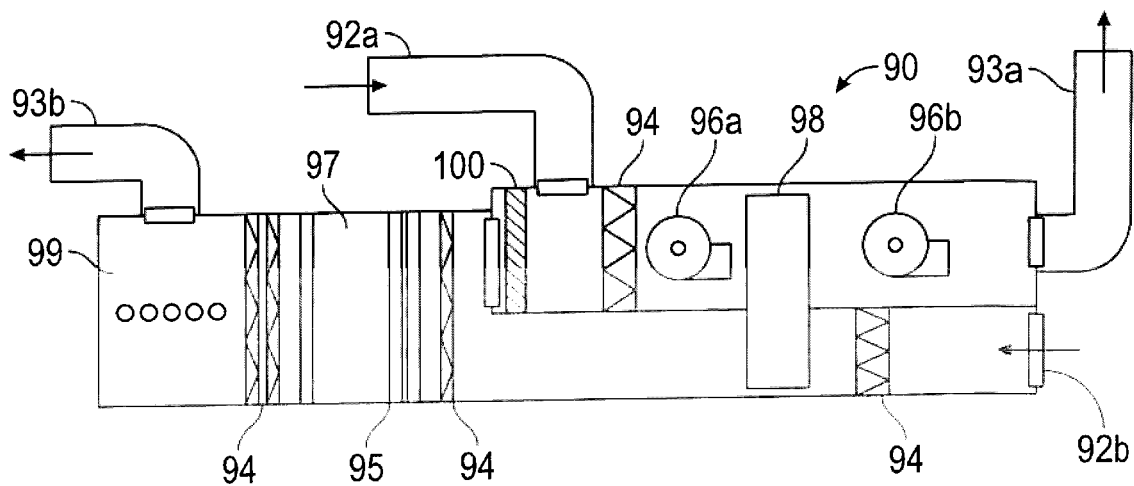

Also for example, FIG. 2E illustrates an air handling system 90 used in a cruise ship having a detoxification device 100 of the present disclosure. As shown, return/relief air pulled through a return duct 92a is diverted through filters 94 by blowers 96a, which force the air through a heat wheel 98. Additional blowers 96b then pass air out an exhaust 93a to the atmosphere.

Meanwhile, outside air entering intake 92b passes through filters 94, and the other end of the heat wheel 98 before passing on to cooling and filtering elements. At the return duct 92a, the return/relief air is also diverted to the cooling and filtering elements. For these elements, the air is passed through one or more of filters 94, cooling coils 95, UV light treatment 97, additional filters 94, and a steam humidification treatment 99 before passing out to supply air ducts 93b.

As shown in FIG. 2E, the detoxification device 100 can be used in the return air from the return duct 92a that is recycled back through the system 90. Throughout the cruise ship, various components are used for conducting the air, including duct heaters, axial fans, dampers, etc. Various self-contained unit heaters can also be used in different areas of the cruise ship. As similarly disclosed with respect to the facility, the detoxification device 100 can be incorporated into the various returns, ducts, vents, and standalone units used throughout the vessel.

As will be appreciated, other vehicles and mass transit systems having air handling systems can benefit in a similar way to an airplane and a cruise ship. For example, busses, trains, and subways used in mass transit have air handling systems that typically use both outside air and recycled air. The disclosed detoxification device 100 can be incorporated into these air handling systems in a comparable way to those discussed above.

In some embodiments, the detoxification device 100 is used with control circuitry and supplied power. For example, the control circuitry may include a local controller 200 having appropriate power circuitry and processing circuitry for powering and controlling the operation of the detoxification device 100. In some embodiments, the controller may receive a signal enabling the controller 200 to determine (e.g., independently) if air flow is being conducted through the HVAC system 20 and transmitted via the detoxification device 100. Alternatively, in some embodiments, the local controller 200 can be integrated and/or in signal communication with a system controller 50 for the HVAC system 20, such that the controller 200 may cause the system controller 50 to control activation of the HVAC system 20 conduct air through the HVAC system 20 and transmitted the detoxification device 100. In other alternative embodiments, the detoxification device 100 may lack local controls and may be centrally controlled by the system controller 50. As will be appreciated, these control arrangements can be used in any combination throughout a facility 10, multiple detoxification devices 100, conditioning zones, HVAC components, and the like.

Figures 3A, 3B:
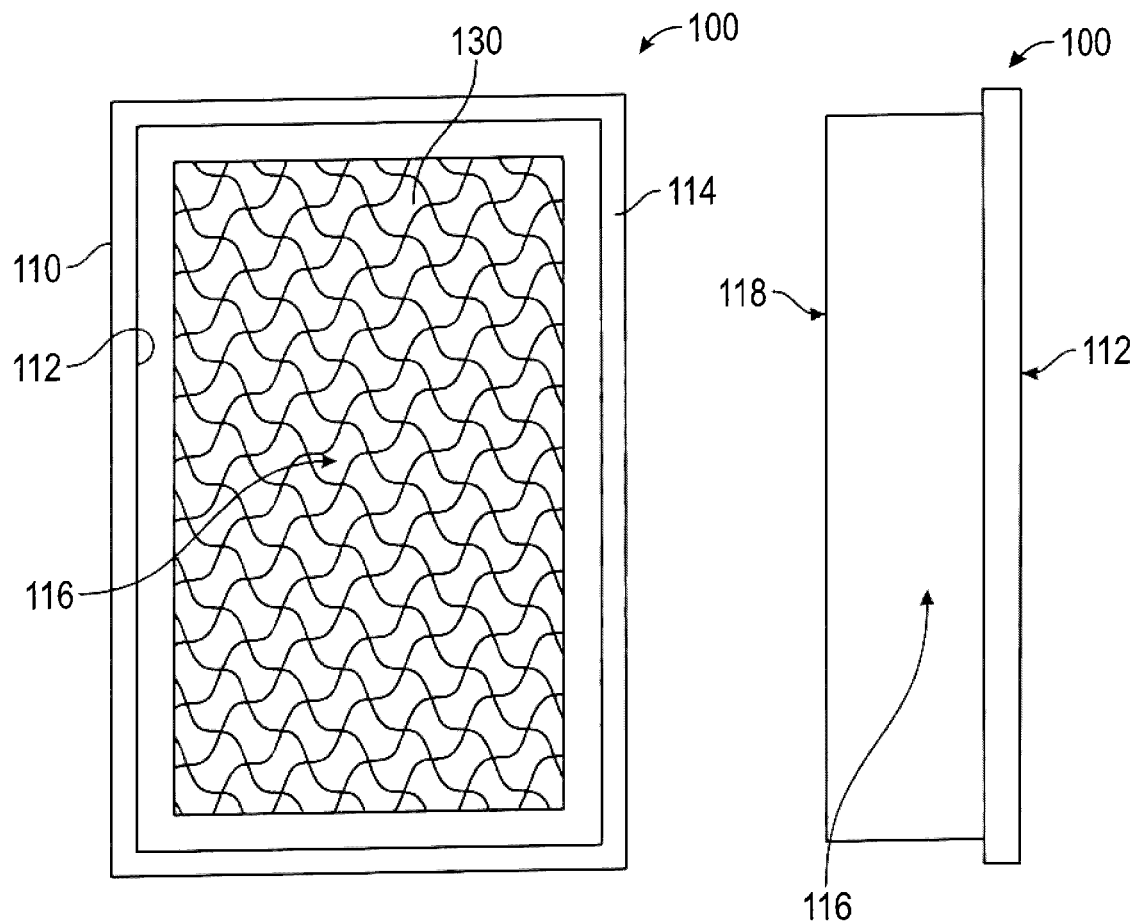
FIGS. 3A, 3B, and 3C illustrate front, side, and end views of a detoxification device of the present disclosure.
Figure 3C:
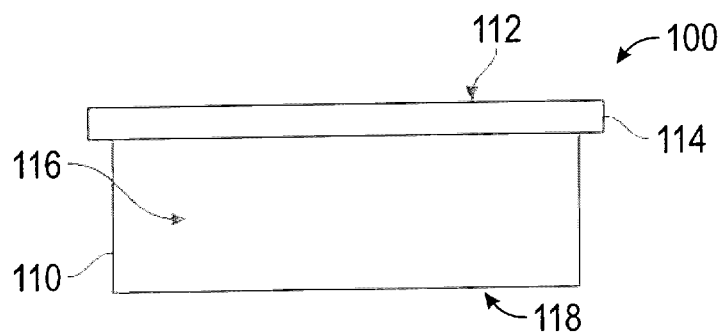

Referring to FIGS. 3A, 3B, and 3C, front, side, and end views of an example embodiment of the detoxification device 100 of the present disclosure are illustrated. In the illustrated embodiment, the detoxification device 100 generally includes a frame 110 generally defining a plenum 116, a heating element 120 disposed within the plenum 116, and a filtration media 130 generally disposed across the plenum 116.

The frame 110 may be generally configured to retain the heating element 120 and the filtration media 130 in position within the plenum 116, for example, extending across the plenum 116 generally perpendicular to the direction of air-flow through the plenum 116. The frame 110 may also be configured to allow the detoxification device 100 to be inserted into and/or disposed within a HVAC system, such as within an air return of as illustrated in FIG. 1, for replacing an existing return altogether, or to be disposed at another location within the HVAC system 20 such as illustrated in FIGS. 2A, 2B, and/or 2C.

The frame 110 may generally include a plurality of sidewalls. For example, in the embodiment of FIGS. 3A, 3B, and 3C, the frame 110 includes four sidewalls cooperatively at least partially enclosing the plenum 116, which generally defines a flow-space for air intended to move through the detoxification device 100. The plenum 116 may be exposed on opposing open ends thereof, for example, at an inlet 112 and an outlet 118, respectively of the plenum 116. In some embodiments, such as illustrated in FIG. 1, the inlet 112 may include a rim 114, which may be configured to engage opening within which the frame 110 is disposed. Additionally or alternatively, fasteners can be used to affix the rim to surrounding structures. The overall dimensions may vary according to the position within the HVAC system where the detoxification device will be disposed.

Generally, the heating element 120 is configured to be heated. For example, in some embodiments, the heating element 120 comprises and/or is formed from an electrically-conductive material that exhibits a resistance such that the application of an electrical current to the heating element 120 causes the heating element 120 to generate heat.

In some embodiments, the heating element 120 comprises of a metallic foam. For example, the heating element 120 may comprise or consist of a foam formed from stainless steel (e.g., SAE 304 stainless steel). Additionally or alternatively, in some embodiments the heating element 120 may comprise or consist of a foam formed from a metal comprising nickel, titanium, molybdenum, copper, aluminum, carbon, nitrogen, silicon, sulfur, selenium, niobium, and alloys thereof. In various embodiments, the metallic foam may comprise at least 95% by weight, alternatively, at least 96% by weight, alternatively, at least 97% by weight, alternatively, at least 98% by weight, alternatively, at least 99% by weight, alternatively, at least 99.5% by weight of the metal. Additionally or alternatively, in some embodiments the heating element comprises a mesh, a woven cloth, or a nonwoven cloth, for example, a stainless steel mesh or a carbon cloth.

In some embodiments, the heating element 120 (e.g., a stainless steel foam) may be characterized as electrically conductive and as exhibiting an electrical resistivity from about $6.8 \times 10^{-7}$ Ω·m (ohm-meter) to about $7.2 \times 10^{-7}$ Ω·m. In some embodiments, the heating element 120 (e.g., a stainless steel foam) may be characterized as exhibiting a resistance of from about 4Ω (ohms) to about 20Ω where the voltage applied is 110 V or a resistance of from about 8Ω to about 20Ω where the voltage applied is 220 V, for example, such that the current drawn by the heating element 120 is from about 5 A (amps) to about 30 A. When a current is passed through the heating element 120, the resistance exhibited by the heating element 120 causes the heating element 120 to be heated to a target temperature, for example, which may be hot enough to kill pathogens, including COVID-19. In various embodiments, the target temperature may be at least 75° C., alternatively, at least 100° C., alternatively, at least 125° C., alternatively, at least 150° C., alternatively, at least 175° C., alternatively, at least 200° C., alternatively, at least 225° C., alternatively, at least 250° C. For example, in various embodiments, the heating element 120 may reach the target temperature within about 30 seconds of the current being passed through the heating element 120, alternatively, within about 10 seconds, alternatively, within about 5 seconds, alternatively, within about 4 seconds, alternatively, within about 3 seconds, alternatively, within about 2 seconds, alternatively, within about 1 seconds, alternatively, within less than a second, alternatively, within about half of a second, of the current being passed through the heating element 120.

Also, in some embodiments, the heating element 120 may be configured to allow air-flow through one or more dimensions of the heating element. For example, the heating element 120 may be characterized as permeable to air, such that air is able to flow through the heating element. For example, in embodiments where the heating element 120 comprises a metallic foam the (e.g., a stainless steel foam), the heating element 120 may be characterized as porous. For example, the metallic foam may include a plurality of pores interspersed through the metallic foam.

In some embodiments, the metallic foam may comprise a plurality of open-cell pores and/or a plurality of closed-cell pores. For example, in some embodiments, at least about 50%, alternatively at least about 60%, alternatively, at least about 70%, alternatively, at least about 80%, alternatively, at least about 90%, alternatively, substantially all of the pores may be characterized as open-cell pores. For example, in some embodiments, the metallic foam may be characterized as a reticulated foam. The metallic foam may have a porosity ranging from about 80 pores/in$^2$ (pore per square inch) to about 120 pores/in$^2$, for example, a porosity of about 100 pores/in$^2$. The pores may be regularly distributed through the metallic foam and may have a diameter ranging from about 0.10 mm to about 0.20 mm, for example, a diameter of about 0.15 mm. The presence of pores within the metallic foam may give the heating element 120 (e.g., a metallic foam) a density in the range of from about 5.0 g/cm$^3$ to about 6.5 g/cm$^3$, for example, about 5.69 g/cm$^3$ for a metallic foam of SAE 304 stainless steel. The pore sizes and free volume of the metallic foam may be varied according to desired parameters. For example, as will be disclosed herein, the distribution of pores, including open cell pores, may be effective to form three-dimensional channels (e.g., flow-paths) effective to allow the passage of air through the heating element 120.

In some embodiments, the heating element 120 may be configured to, when heated, impart heat to the filtration media 130. For example, the heating element 120 may have a configuration effective to increase the surface area of the heating element 120 exposed and/or in contact with the filtration. Not intending to be bound by theory, an increase in the surface area of the heating element 120 relative to its volume may be effective to improve heat transfer to the filtration media 130 or to improve the efficiency with which heat may be transferred from the heating element 120 to the filtration media 130.

Figure 5:
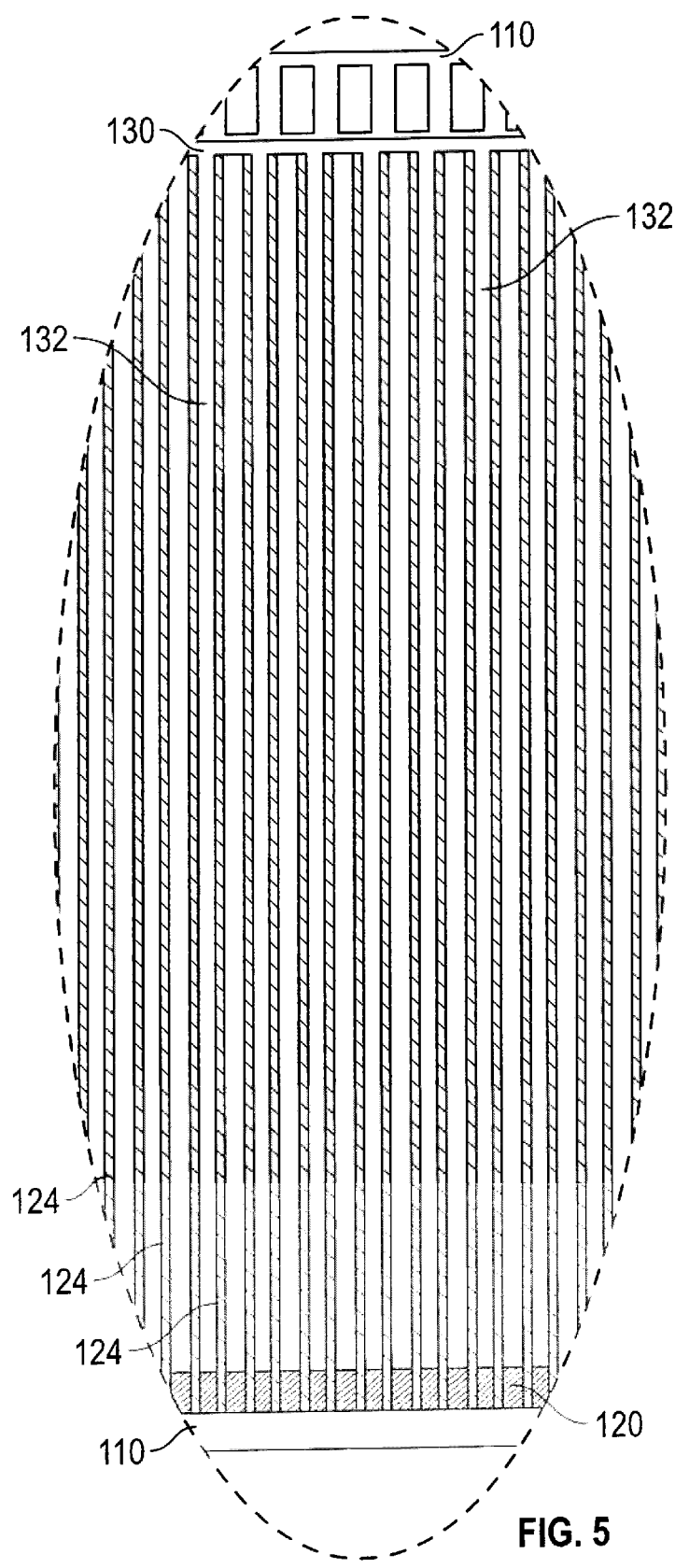
FIG. 5 illustrates a detailed cutaway view of a detoxification device of the present disclosure.

For example, referring to FIGS. 4 and 5, and cutaway of perspective view of an embodiment of the detoxification device 100 and a detailed cutaway view of a portion of the detoxification device 100, respectively, showing the heating element 120 is shown. As illustrated in the embodiment of FIGS. 4 and 5, the heating element 120 generally includes a base portion 122 and a plurality of fins 124 extending generally perpendicular to the base portion 122. In various embodiments, each of the base portion 122 and the plurality of fins 124 may have a suitable thickness, for example, from a thickness of from about 0.5 mm to about 2.0 mm. Also, in various embodiments, the base portion 122 and one or more of the plurality of fins 124 may be formed from one or more layers (e.g., one or more layers of a metallic foam), which may be coupled by welding, adhesive, or by folding. In the embodiment of FIGS. 4 and 5, the plurality of fins 124 are illustrated as being corrugated, which may be effective to further increase the surface area of the heating element 120, although in other embodiments the fins may be flat.

The plurality of fins 124 may extend generally parallel to one-another and may be spaced apart from one another, thereby at least partially defining a plurality of void-spaces between adjacent fins 124.

In some embodiments, the filtration media 130 may be configured to catch and retain particles larger than about 0.3 μm with an efficiency of at least 99.97%. For example, the filtration media 130 may be characterized as meeting those filtration standards associated with HEPA filtration, for example, the filtration media 130 may be characterized as a HEPA filter. In some embodiments, the filtration media 130 may include a plurality of pores having a diameter of less than 1 μm, for example, a diameter from about 0.05 μm to about 1 μm.

The filtration media 130 may be formed from any material suitable for filtration and for withstanding the heat transmitted from the heating element 120. For example, in some embodiments the filtration media 130 may be capable of withstanding temperatures of at least at least 200° C., alternatively, at least 225° C., alternatively, at least 250° C., without degradation or diminishment of its filtration capacity.

In various embodiments, the filtration media 130 may be formed from any suitable material or combination of materials, examples of which may include non-woven, randomly-arranged fibers such as fiberglass, expanded polytetrafluoroethylene (ePTFE) fibers, and the like.

Additionally, in some embodiments, one or more surfaces of the detoxification device 100, or a component thereof, may include an anti-microbial coating to eliminate live bacteria and viruses. For example, the filtration media 130 may include an anti-microbial coating to eliminate pathogens trapped by the filter media. Additionally or alternatively, the inside walls of the frame's plenum 116 may also have anti-microbial coating.

In the embodiment of FIGS. 4 and 5, the heating element 120 and the filtration media 130 may be disposed within the frame 110, for example, across the plenum 116, perpendicular to the direction of air-flow through the plenum 116. The filtration media 130 may be disposed toward an upstream side of the frame 110, for example, toward or adjacent the inlet 112 of the plenum 116 and the heating element 120 may be disposed downstream side of the frame 110, for example, toward or adjacent the outlet 118 of the plenum 116. The heating element 120 and filtration media 130 may be fixed to the frame 110 via any suitable engagement. In some embodiments, one or more insulating materials may be disposed between the heating element 120 and the frame 110. The insulating material(s) may be effective to impede heat transfer between the heating element 120 and the frame 110 and/or to provide electrical insulation such that a current applied to the heating element 120 does not reach the frame 110.

In some embodiments, the filtration media 130 may be continuous and may include a plurality of pleats 132. As shown in FIG. 5, the pleats 132 may be disposed within the void-spaces between two adjacent fins 124 of the heating element 120. In various embodiments, the filtration media 130 may include from 1 to 10 pleats 132 per inch and the pleats may have a height of from about one (1) inch to about 12 inches. For example, in some embodiments the pleats 132 may be effective to increase the effective surface area of the filtration media 130 relative to the area of the plenum 116 defined by the frame 110. For example, in various embodiments, the pleats 132 may yield an effective surface area for the filtration media 130 that is at least about 500% of the area of the plenum 116, alternatively, at least 1,000% of the area of the plenum 116, alternatively, at least 1,200% of the area of the plenum 116, alternatively, at least 1,400% of the area of the plenum 116, alternatively, at least 1,600% of the area of the plenum 116, alternatively, at least 1,800% of the area of the plenum 116, alternatively, at least 2,000% of the area of the plenum 116, alternatively, at least 2,500% of the area of the plenum 116.

Not intending to be bound by theory, the pleats 132 may increase the surface area through which air may move through the filtration unit and, thereby, improve air flow. For example, the detoxification device 100 may exhibit a pressure drop in the range of from about 0.5 inches to about 3 inches of water column height while allowing air flow, per square foot of cross-sectional area of the plenum 116, in the range of from about 100 cubic feet per minute (CFM) to about 1,000 CFM.

Further, and again not intending to be bound by theory, the pleats 132 may increase the surface area with which a pathogen might come into contact. Further still, and again not intending to be bound by theory, the pleats 132 may also improve heat transfer and/or the efficiency of heat transfer between the heating element 120 and the filtration media 130, for example, by increasing contact and proximity between the filtration media 130 and the heating element 120.

Figure 6:
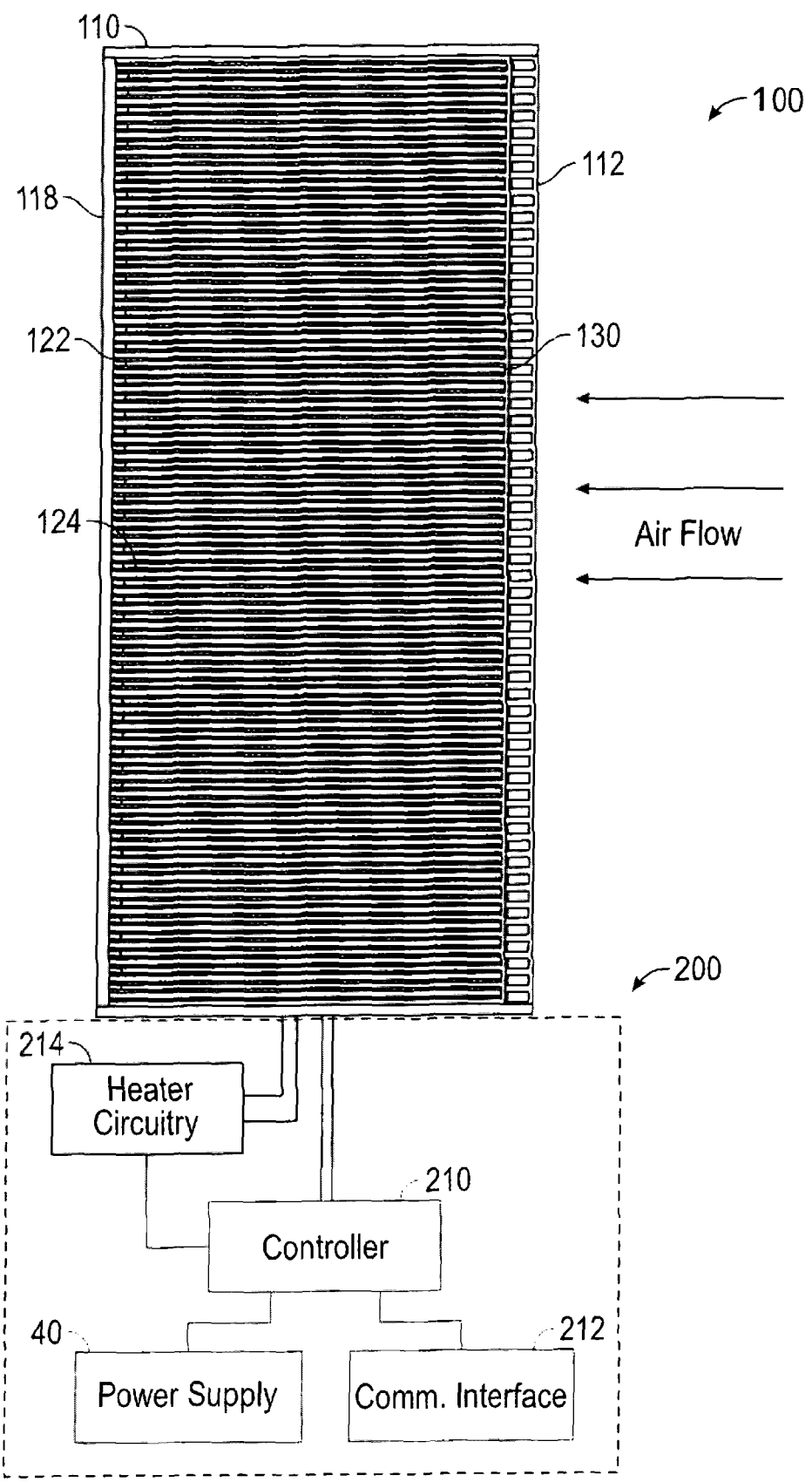
FIG. 6 illustrates a heating arrangement having a plurality of electric elements disposed in a plenum of a frame and connected to a power source control.

Referring to FIG. 6, the operation and/or control of the detoxification device 100, for example, via the controller 200, is illustrated. In some embodiments, the controller 200 can be connected to one or more types of power supply(s) 40, such as available AC power supplies of a facility, battery power, or other power source. Power circuitry of the controller 200 can convert the supplied power as needed to produce DC power and voltage levels. The heating element 120 is connected in electrical communication with the power supply 40 through the controller 200, which controls operation of the heating element 120 in the plenum 116. For example, the controller 200 may be configured to control the heating of the heating element 120 by regulating the power supplied to the heating element.

Generally, the controller may be configured to determination whether if air flow is being conducted through the HVAC system 20 and, based upon that determination, operate the heating element 120 so that the heating element 120 is heated while air flow is not being conducted through the HVAC system. Alternatively, in some embodiments, the controller may be configured to operate the heating element 120 so that the heating element 120 is heated while air is flowing through the HVAC system.

In some embodiments, the controller 200 may receive a signal enabling the controller 200 to determine if air flow is being conducted through the HVAC system 20 and transmitted via the detoxification device 100.

For example, in some embodiments, the controller 200 can include or be in signal communication with one or more sensors. The controller 200 may be in signal communication with a flow sensor 217 configured to indicated parameters such as flow and/or velocity of the air passing through the plenum 116. The detected flow by the flow sensor 217 may be used by the controller 200 to initiate operation of the detoxification device 100. In some embodiments, the controller 200 may be configured to cause the heating element 120 to be heated when the flow sensor 217 indicates that there is no air flow through the plenum 116 or, alternatively, when the flow sensor 217 indicates that air flow through the plenum 116 is less than an air-flow threshold.

Additionally or alternatively, in some embodiments, the controller 200 can be integrated and/or in signal communication with other detoxification devices and with other components of an air handing system in a facility, such as the system controller 50 for the HVAC system 20. For example, the controller 200 may include a communication interface 212 to communicate with the system controller 50. For example, the controller 200 can receive signals indicative of whether the HVAC system 20 is on/off, which may be indicative of the passage of the air flow through the detoxification device 100. The controller 200 can then the control the heating of the heating element 120 based on the signals received.

Alternatively, in some embodiments, the controller 200 can be integrated and/or in signal communication with a system controller 50 such that the controller 200 may cause the system controller 50 to control activation of the HVAC system 20 conduct air through the HVAC system 20 and transmitted the detoxification device 100.

In other alternative embodiments, the detoxification device 100 may lack local controls and may be centrally controlled by the system controller 50. As will be appreciated, these control arrangements can be used in any combination throughout a facility 10, multiple detoxification devices 100, conditioning zones, HVAC components, and the like.

In some embodiments, based upon the determination of whether or not air flow is being conducted through the HVAC system 20 and, the controller 200 may cause the heating element 120 to be heated and, the heating element 120 may cause the filtration media 130 to be heated. For example, during at least a portion of a time during the controller 200 is signaled that air is not being conducted through the HVAC system 20 and/or through the detoxification device 100, the controller 200 may cause the heating element 120 and/or the filtration media 130 to be heated to a target temperature. Alternatively, in some embodiments, the controller 200 may cause the heating element 120 and/or the filtration media 130 to be heated to a target temperature while air is being conducted through the HVAC system 20 and/or through the detoxification device 100.

For example, in some embodiments, the controller 200 may be disposed in electrical communication with heater circuitry 214 connected to the heating element 120. In some embodiments where the controller 200 determines that air is not passing through the detoxification device 100 (for example, the HVAC system is not being operated), the controller 200 can cause the heating element 120 to be heated, for example, via the heater circuitry 214 and the power supply 40. As will be appreciated, the controller 200 and heater circuitry 214 may include any necessary switches, relays, timers, power transformers, etc. to condition and control power supplied to the heating element 120.

Also, for example, the controller 200 can include or be in signal communication with one or more temperature sensors 216 disposed in the plenum 116 adjacent the heating element 120. The temperature sensor(s) 216 may be configured to measure temperature associated with the heating element 120 and/or the filtration media 130 so that the controller 200 can operate the heating element 120 to cause the heating element 120 and/or the filtration media 130 to reach the target temperature. Depending on the implementation and the pathogens to be affected, the heating element 120 and/or the filtration media 130 can heated to the surface temperature effective to kill a particular pathogen. For example, a temperature of about 56° C. or above (133-152° F.) may be effective to kill the SARS coronavirus. For example, in various embodiments, the heating element 120 and/or the filtration media 130 can be heated to the surface temperature of at least about 75° C., alternatively, at least 100° C., alternatively, at least 125° C., alternatively, at least 150° C., alternatively, at least 175° C., alternatively, at least 200° C., alternatively, at least 225° C., alternatively, at least 250° C.

In various embodiments, the controller 200 may also be configured to maintain the heating element 120 and/or the filtration media 130 at the target temperature for a duration effective to kill the pathogen. For example, in various embodiments, the controller 200 may also be configured to maintain the heating element 120 and/or the filtration media 130 at the target temperature for a duration from about 0.5 seconds to about 30 second, alternatively, from about 0.75 seconds to about 20 second, alternatively, less than about 15 second, alternatively, less than about 10 second, alternatively, less than about 5 second, alternatively, more than about 0.25 second, alternatively, more than about 0.5 seconds, alternatively, more than about 0.75 second, alternatively, more than about 1.0 seconds, alternatively, more than about 2.0 seconds, alternatively, more than about 3.0 seconds, alternatively, more than about 4.0 seconds.

Although the detoxification device 100 has been described above as including a frame 110 that accommodates an air filter in the frame 110, in some embodiments, the detoxification device 100 can include a frame 110 configured to be mounted behind a conventional air return. Alternatively, the detoxification device 100 can include a frame 110 that mounts at an intake of a furnace downstream from a separate air filter. In these types of arrangement, the detoxification device 100 can include a frame 110, and a heating element 120 as before.

Although various embodiments of the detoxification device 100 have been disclosed as being used separately or in combination with an air handling system, in some other embodiments, a detoxification device including a filtration media and a heating element controlled by control/power circuitry can be configured to be retrofitted or added to an existing duct of the air handling system. For example, such a detoxification device can be disposed upstream of operable components of the air handling system, or can be configured elsewhere in the air flow.

Also, in some other embodiments, a detoxification device including a filtration media and a heating element controlled by control/power circuitry can be incorporated into more stand-alone detoxification devices arranged in a facility. These stand-alone detoxification devices may have local controllers and user/communication interfaces, and can be controlled individually or commonly.

Although the embodiment of FIG. 1 illustrates the detoxification device 100 implemented within a HVAC system 20 disposed within a facility 10, in other embodiments the detoxification device 100 may be implemented in the context of (e.g., incorporated into) a mobile detoxification device used to detoxify and/or purify the air in a facility. Briefly, the mobile detoxification device may include a housing that is mobile in the environment and that has an intake and an exhaust. The mobile detoxification device may have on or more detoxification devices, as disclosed herein, and one or more prime movers. The detoxification devices may be disposed toward the intake. For mobility, the mobile housing may also include one or more caster wheels, a tow hitch, and/or a handle.

The intake can be an open side of the housing for intaking environmental air across a larger surface area, while the exhaust can be a port out of the top of the housing directing treated air in an upper area of the environment. The housing may have sidewalls enclosing an interior or main plenum for passage of air flow therethrough from the intake to the exhaust. The one or more prime movers may be disposed in the housing between the intake and the exhaust and may be operable to draw in the air from the environment through the intake and exhaust treated air back to the environment through the exhaust.

The mobile detoxification device can be controlled a local controller, which determines independently the device's operation. Alternatively, the local controller can be integrated with a system controller for an HVAC system (e.g., the HVAC system 20). In a further alternative, the mobile detoxification device may lack local controls and may be centrally controlled by a system controller or a remote controller. As will be appreciated, these control arrangements can be used in any combination throughout a facility, multiple detoxifications devices, conditioning zones, and the like.

The detoxification device, as disclosed herein, may be advantageously employed to detoxify and/or purify air within various facilities of the types discussed herein, for example, by removing pathogens from the air. For example, in various embodiments, the detoxification device 100 can be effective to detoxify and/or purify at least 100 CFM, or at least 500 CFM, or at least 1,000 CFM, at least 5,000 CF, at least 10,000 CFM, at least 20,000 CFM, or at least 30,000 CFM depending upon the particular configuration of the detoxification device.

For example, as disclosed herein, the filtration media 130 within the detoxification device 100 may be effective to catch at least 99%, or at least 99.5%, or at least 99.95%, or at least 99.97% of all particles within air flowing through the detoxification device 100 (e.g., air moving via the HVAC system 20), including any pathogens, such as the Sars-CoV-2 virus. In operation, pathogens present within air in a facility may be circulated through the HVAC system and through the detoxification device 100 and may be caught and/or trapped by the filtration media 130. As disclosed herein, when the controller 200 determines that the HVAC system is not operating to move therethrough (e.g., when the HVAC system cycles "off"), the controller 200 will direct power to the heating element 120 necessary to cause the heating element 120 and/or the filtration media 130 to the target temperature. As the heating element 120 is heated, heat is transmitted to the filtration media 130 where any pathogens are caught, killing the pathogens.

As such, the heating element 120 (e.g., a metal foam) provides heat effective to eliminate pathogens but, at the same time, because of the porosity of the heating element 120 (e.g., a metal foam), the heating element 120 does not overly impede the air flow and does not detrimentally increase the energy required from the HVAC system to move air through the detoxification device 100 (e.g., in comparison to a conventional HEPA filter).

Moreover, implementation of the detoxification device 100 does not significantly or detrimentally alter the temperature of the air being purified. Particularly, and as disclosed herein, the controller 200 does not cause the heating element 120 to be heated while the HVAC system 20 is being operated; that is, the heating element 120 is only heated while air is not flowing through the HVAC system 20. Because the heating element 120 is only heated while air is not flowing through the HVAC system 20, heat is not dissipated to air moving through the HVAC system. As such, less energy is needed to heat the heating element 120 and/or filtration media 130 to the target temperature and, also, the air is not detrimentally heated. As such, the heat directed to the heating element 120 will be used to kill pathogens rather than increase the air temperature, meaning that increases in air temperature will be minimized.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A detoxification device for removing pathogens from air within an environment, the detoxification device comprising:
    a filtration media configured to catch and retain particles larger than about 0.3 micrometers (μm) with an efficiency of at least 99%;
    a heating element comprising a metallic foam, wherein the heating element is configured to be heated upon application of an electrical current to the heating element, and wherein the heating element is configured, upon being heated, to heat the filtration media to a target temperature that is effective to kill a pathogen; and
    a controller in electrical communication with the heating element, the controller being configured to cause the heating element to be heated when the controller determines that air flow is not being conducted through the detoxification device.

2. The detoxification device of claim 1, wherein the filtration media comprises fiberglass or expanded polytetrafluoroethylene (ePTFE) fibers.

3. The detoxification device of claim 1, wherein the filtration media includes a plurality of pores having a diameter from about 0.05 μm to about 1 μm.

4. The detoxification device of claim 1, wherein the filtration media is characterized as withstanding a temperature of at least 200° C. without degradation or diminishment of its filtration capacity.

5. The detoxification device of claim 1, wherein the metallic foam comprises an alloy comprising at least 99% by weight of an alloy comprising chromium and nickel.

6. The detoxification device of claim 5, wherein the alloy is stainless steel.

7. The detoxification device of claim 1, wherein the metallic foam includes a plurality of open-cell pores a least partially defining a plurality of flow-paths through the heating element.

8. The detoxification device of claim 1, wherein the metallic foam exhibits a porosity of from about 80 pores per square inch to about 120 pores per square inch.

9. The detoxification device of claim 1, further comprising a frame having a plurality of sidewalls at least partially defining a plenum.

10. The detoxification device of claim 1, wherein the heating element and the filtration media extend across a plenum of the detoxification device generally perpendicular to a direction of air-flow through the plenum, wherein the filtration media is disposed toward an inlet to the plenum and the heating element is disposed toward an outlet of the plenum.

11. The detoxification device of claim 10, wherein the heating element comprises a base portion and a plurality of fins extending perpendicularly from the base portion thereby at least partially defining a plurality of void-spaces between the fins.

12. The detoxification device of claim 11, wherein the filtration media comprises a plurality of pleats.

13. The detoxification device of claim 12, wherein the each of the plurality of pleats is disposed within one of the plurality of void-spaces between the fins.

14. The detoxification device of claim 13, wherein the detoxification device exhibits a pressure drop in the range of from about 0.5 inches to about 3 inches of water column height while allowing air flow, per square foot of cross-sectional area of the plenum, in the range of from about 100 cubic feet per minute (CFM) to about 1,000 CFM.

15. The detoxification device of claim 1, wherein the controller is configured to cause the heating element to be heated based upon determining if air flow is being conducted through the detoxification device.

16. The detoxification device of claim 1, wherein the detoxification device is configured to be incorporated into a heating, ventilating, and air conditioning (HVAC) system disposed within a facility.

17. The detoxification device of claim 1, wherein the detoxification device is configured to be incorporated into a mobile detoxification device having a housing, an intake, and an exhaust.

18. A method for removing pathogens from within an environment, the method comprising:
    determining that air flow is not being conducted through a detoxification device, the detoxification device comprising:
        a filtration media configured to catch and retain particles larger than about 0.3 micrometers (μm) with an efficiency of at least 99%; and
        a heating element comprising a metallic foam; and
    based upon the determination that air flow is not being conducted through the detoxification device, heating the heating element so that, upon the heating element being heated, the filtration media is heated to a target temperature that is effective to kill a pathogen.

* * * * *